(12) United States Patent
Heineke et al.

(10) Patent No.: US 6,197,720 B1
(45) Date of Patent: Mar. 6, 2001

(54) PALLADIUM CLUSTERS AND THEIR USE AS CATALYSTS

(75) Inventors: Daniel Heineke, Maikammer; Ekkehard Schwab, Neustadt; Martin Fischer, Ludwigshafen; Guenter Schmid, Marburg; Monika Baeumle, Essen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/197,681

(22) Filed: Nov. 23, 1998

(30) Foreign Application Priority Data

Dec. 2, 1997 (DE) ............................................ 197 53 464

(51) Int. Cl.$^7$ .................................................. B01J 23/42
(52) U.S. Cl. ...................... 502/325; 502/339; 502/344; 585/275; 252/302; 556/16; 556/136
(58) Field of Search .................... 556/16, 136; 252/302; 502/325, 339, 344

(56) References Cited

U.S. PATENT DOCUMENTS 5,147,841    9/1992    Wilcoxon ............................ 502/173

FOREIGN PATENT DOCUMENTS

| 2207027 | 6/1996 | (CA) . |
| 2238253 | 11/1998 | (CA) . |
| 4412463 | 10/1995 | (DE) . |
| 4443705 | 6/1996 | (DE) . |
| 19506113 | 8/1996 | (DE) . |
| 879642 | 11/1998 | (EP) . |
| 96/26004 | 2/1995 | (WO) . |
| 97/24224 | 7/1997 | (WO) . |

OTHER PUBLICATIONS

Chem Abstract Online 1996:516448, 1996 month unavailable, abstract of DE 4443705.*
*J. Am. Chem. Soc.*, vol. 115, 1993, pp. 2046–2048.
*J. Am. Chem. Soc.*, vol. 116, 1994, pp. 7401–7402.
*Chinese J. of Reactive Polymers*, vol. 1, No. 1, 1992, pp. 48–53, months unavailable.

\* cited by examiner

*Primary Examiner*—Samuel Barts
(74) *Attorney, Agent, or Firm*—Keil & Weinkauf

(57) ABSTRACT

The invention relates to colloidal palladium composed of palladium clusters with an average particle diameter 0.2 nm$\leq$d$\leq$2 nm with at least 80% of the palladium clusters having a particle diameter which differs by not more than 0.2 nm from the average particle diameter d, it being possible for the palladium clusters to have protective ligands on the surface.

The invention further relates to a process for preparing a colloidal solution of palladium by reacting a palladium salt with a reducing agent in solution at from 0 to 300° C., employing a branched-chain alcohol as reducing agent and phosphines and/or aromatic nitrogen compounds as protective ligands.

The invention further relates to palladium-containing heterogeneous catalysts comprising colloidal palladium applied to a carrier, and to a process for their preparation.

16 Claims, No Drawings

PALLADIUM CLUSTERS AND THEIR USE AS CATALYSTS

The invention relates to colloidal palladium composed of palladium clusters, a rocess for its preparation, its use, colloidal palladium-containing heterogeneous atalysts, a process for their preparation, and their use.

Metal colloids are systems in which metal particles with a diameter of the order of about 1 nm to 1 $\mu$ are present. The extremely fine-particle metal itself is referred to as colloidal metal. It may be in undiluted form, dispersed in a continuous phase or adsorbed at a phase boundary. A dispersion thereof in a solvent is referred to as a colloidal solution of the metal.

By metal clusters are meant metal particles which consist of only a few, up to a few thousand, metal atoms and are at the lower end of the abovementioned scale of sizes for colloidal metal.

The preparation of metal colloids has been known for a long time. Normally, metal salts are reduced in solution in the presence of stabilizers to the metal. The stabilizers are substances which are able to coordinate with the metal and thus protect it from agglomeration. It is also known that properties such as size and size distribution of the formed colloidal particles are influenced inter alia by the choice of the reducing agent and of the protective ligand, the ratio of the protective ligand to the metal ion, the solvent and the anion present in the metal salt. However, control of the particle size is not possible because of the complex mechanism of formation; on the contrary, reliance on empirical optimization is necessary.

Metal colloids from noble metals such as palladium are employed on a large scale as catalysts. For these, particularly small particle sizes are desirable because for the same amount of catalyst the catalyst surface area available increases in inverse proportion to the particle diameter. The activity of the catalysts is therefore usually directly related to the size of the catalytically active metal particles.

A number of reactions catalyzed by metal colloids also display the phenomenon of structural sensitivity, i.e. the selectivity of the reaction is related to the size of the catalytically active particles. In order to be able to exploit this effect, the catalyst particles must show a narrow size distribution.

DE-C 44 12 463 describes the preparation of colloidal solutions of palladium by reducing palladium salts with a number of reducing agents such as phosphites, hypophosphites, boranes, ascorbic acid, hydrazine and formaldehyde in the presence of protective colloids, employing as protective colloids polymers such as polyvinylpyrrolidone, poyvinylpyridine, polyvinyl methyl ketone, polyvinyl alcohol, polyvinyl acetate, polyacrylate, alkyl- and hydroxyalkylcelluloses. The publication contains no information on the particle size and its distribution. However, it is known that palladium colloids prepared by this method have a very wide distribution, with particle sizes in the range from a few nm up to about 50 nm.

Chinese Journal of Reactive Polymers 1 (1992), 48-53 discloses the preparation of colloidal palladium by reducing palladium(II) chloride in methanol in the presence of poly-N-vinyl-2-pyrrolidone as protective ligand with methanol/NaOH as reducing agent. Palladium particles with a diameter of from 1 to 3 nm and an average diameter of 2 nm are obtained. The disadvantage of this process is the use of palladium chloride because chloride can act as catalyst poison. In addition, polymeric protective ligands have a strong shielding effect and can be removed only with difficulty.

J. Am. Chem. Soc. 115(1993), 2046–48 describes the preparation of colloidal palladium by reducing palladium(II) acetate with hydrogen in the presence of phenanthroline as protective ligand. 90% of the resulting clusters have a particle size from 3.15 to 3.6 nm. The process requires the use of gaseous hydrogen as reducing agent, which complicates the chemical and safety engineering.

J. Am. Chem. Soc. 116(1994) describes the electrolytic preparation of palladium clusters. This entails the nobel metal in the form of a foil undergoing anodic oxidation and cathodic reduction to palladium(0), employing conductive tetraallkylammonium salts as stabilizer. The resulting palladium colloids have an average particle size which varies in the nanometer range depending on the current density used in the electrolysis, and have a relatively wide distribution of particle sizes. The process makes uses of physiologically unacceptable organic solvents such as acetonitrile/THF.

It is an object of the present invention to provide colloidal palladium with particles of defined size, in particular with the smallest possible size and a narrow distribution of particle sizes, and moreover to avoid the disadvantages described above.

We have found that this object is achieved by providing colloidal palladium composed of palladium clusters with an average particle diameter 0.2 nm$\leq$d$\leq$2 nm, with at least 80% of the palladium clusters having a particle diameter which differs by not more than 0.2 nm from the average particle diameter, it being possible for the palladium clusters to have protective ligands on the surface.

The object is further achieved by a process for preparing colloidal palladium from a colloidal solution of palladium which is obtained by reacting a palladium salt with a reducing agent in a solution containing the palladium salt, the reducing agent and a protective ligand at from 0 to 300° C., employing a branched-chain alcohol having 4 to 30 carbon atoms, where the longest chain has 3 to 18 carbon atoms, as reducing agent, and employing phosphines and/or aromatic nitrogen bases as protective ligands.

The distribution of the particle diameters of the palladium clusters can be represented mathematically by the following relation:

$$x = d + 0.2 \text{ nm}$$
$$\int [N(x)/N_{tot}] dx \geq 0.8$$
$$x = d - 0.2 \text{ nm}$$

where x is the particle diameter

N(x) is the number of particles with diameter x $N_{tot}$ is the total number of particles and d is the average particle diameter.

The novel colloidal palladium has a particularly narrow particle size distribution. Thus, in general, 80% of the novel palladium clusters have a particle diameter differing by not more than 0.2 nm, preferably by not more than 0.1 nm, from the average particle diameter. It is particularly preferred for 90% of the clusters to have a particle diameter which differs by not more than 0.1 nm from the average particle diameter.

The novel colloidal palladium clusters may comprise one or more other metallic components. Other metallic components which are preferred are metals of main groups III and IV, such as gallium, germanium, tin and lead, and transition metals such as Re, Ru, Os, Rh, Ir, Pt, Ag and Au. These may be present in proportions of from 0.1 to 99% by weight.

The novel palladium clusters may have protective ligands on their surface. The protective ligands prevent agglomeration of the palladium particles formed in the preparation of the colloidal palladium by reducing palladium salt in solution. In general therefore, at least some of the palladium clusters have protective ligands adsorbed on the surface immediately after the reduction of the palladium salt to colloidal palladium. The palladium clusters may still have protective ligands on their surface even at later processing stages, for example after isolation of the colloidal palladium from the colloidal solution of palladium formed and, where appropriate, redispersion in a liquid medium, or else after adsorption of the clusters on a carrier. However, it is possible to remove the protective ligands from the surface of the clusters. This generally requires special measures such as heat treatment of the colloidal palladium.

The colloidal palladium is prepared by initially preparing a colloidal solution of palladium. The colloidal palladium can be isolated from this. The colloidal solution of palladium is prepared by reacting a palladium salt in solution with a reducing agent in the presence of a protective ligand. It has been found that colloidal palladium with a very narrow distribution of particle sizes is obtained on use of branched-chain alcohols as reducing agent.

Preferred reducing agents are unbranched and branched-chain alcohols having 4 to 30 carbon atoms, where the longest chain has 3 to 18 carbon atoms. Preferred alcohols have a boiling point of from 50 to 300° C. Particularly preferred reducing agents have from 1 to 3 branch points and a longest chain having 3 to 18 carbon atoms and, of these, the primary alcohols with only one branch point are particularly preferred. Examples are 2-methylpropanol, 2- and 3-methylbutanol, 2-ethylbutanol, 2-, 3- and 4-methylpentanol, 2- and 3-ethylpentanol and 2-propylpentanol. 3-Methylbutanol is particularly preferred.

All palladium salts can in principle be employed for the preparation, but palladium(II) salts are generally employed. Because the palladium clusters formed are subsequently used as catalysts, the anions should not contain any constituents which may act as catalyst poison. This is why, for example, palladium(II) chloride and palladium(II) sulfate are less preferred. On the other hand, palladium(II) nitrate and palladium(II) salts of carboxylic acids are preferred, and palladium(II) acetate is particularly preferred.

In order to obtain palladium clusters with other metallic components it is possible to use appropriate metal salts such as the salts of the abovementioned metals of main groups III and IV and transition metals.

Compounds which are suitable in principle as protective ligands are those able to coordinate with palladium. Low molecular weight compounds are preferred because these are easier to remove subsequently. Particularly suitable protective ligands are phosphines and aromatic nitrogen compounds. Aromatic nitrogen compounds for the purpose of this invention are aromatic compounds in which the aromatic system has at least one nitrogen atom.

The protective ligands preferably employed are phosphines and aromatic nitrogen compounds which are stable under the reaction conditions. Preferred phosphines are those of the formula $PR^1R^2R^3$, where $R^1, R^2, R^3$, which may be identical or different, are phenyl and cyclohexyl, and said radicals may have substituents. Particularly suitable substituents are groups which increase the water-solubility of the phosphines, such as sulfo and amino groups, which are preferably bonded to a phenyl radical. The presence of such substituents is particularly advantageous when an aqueous solvent is used or it is intended to increase the dispersibility of the palladium clusters in water. Examples are triphenylphosphines which are sulfonated on one or more phenyl rings and have the formula $P(C_6H_5SO_3M)_{3-x}(C_6H_5)_x$ with x=0, 1, 2 and M=alkali metal. Preferred aromatic nitrogen bases are pyridines, bipyridines and phenanthrolines, each of which may be substituted on the aromatic ring by $C_1-C_{18}$-alkyl, $C_5-C_{10}$-cycloalkyl, halogen, hydroxyl, $C_1-C_6$-alkoxy and amino, monoalkyl- and dialkylamino. Particularly preferred protective ligands are triphenylphosphines, especially triphenylphosphine, and phenanthrolines, especially 1,10-phenanthroline, and bipyridines.

The palladium:protective ligand ratio by weight during the synthesis is generally from 100:1 to 1:1000, preferably from 10:1 to 1:100, particularly preferably from 5:1 to 1:15. The optimal palladium:protective ligand ratio also depends on the nature of the protective ligand used. It may, like the choice of the protective ligand, have an effect on the size of the clusters formed. With the abovementioned particularly preferred protective ligands, it is, in particular, from 5:1 to 1:15, specifically from 1:4 to 1:13.

Polar and nonpolar solvents are suitable for synthesizing the palladium clusters. It is possible, for example, to use an aqueous solvent in which the reducing agent is dissolved. The protective ligand which can be employed in this case is the abovementioned sulfonated triphenylphosphine. However, it is also possible to use nonaqueous solvents containing the reducing agent. Examples are alcohols, acetic acid, THF and ethers. In a preferred embodiment of the invention, the reducing agent is used as solvent, in particular employing 3-methylbutanol for this purpose.

The palladium salt is reacted with the reducing agent in general by stirring a solution containing the palladium salt, with or without another metal salt, the protective ligand and the reducing agent at from 0 to 300° C., preferably 20 to 80° C., particularly preferably 50 to 70° C., for a period of a few minutes up to some days, preferably 2 to 10 days, particularly preferably 2 to 7 days. The reaction temperature depends inter alia on the solvent and reducing agent used, and the reaction time is determined inter alia by the protective ligand.

Precipitation and isolation of the colloidal palladium from the colloidal solution of palladium prepared by the process described above is possible by adding a very nonpolar solvent. Examples of suitable very nonpolar solvents are aliphatic, aromatic or cycloaliphatic hydrocarbons having 5 to 10 carbon atoms. The addition of petroleum ether as precipitant has proven particularly suitable. The precipitated colloidal palladium can be isolated by conventional mechanical removal processes, for example by filtration or centrifugation. The novel palladium clusters are stable in air even without diluent so that, after isolation, they can be dried in air.

The novel colloidal palladium can be used as hydrogenation catalyst. Preferred hydrogenation reactions are the hydrogenation of olefins, acetylenes, dienes and saturated and unsaturated nitriles. For this purpose, the isolated colloidal palladium can be redispersed in a liquid medium to give a colloidal solution of palladium. It is also possible to employ the colloidal solutions of palladium obtained from reduction of the palladium salt directly. The novel colloidal palladium can also be applied to a carrier.

The novel colloidal palladium is preferably processed to a palladium-containing heterogeneous catalyst by applying it to a carrier. All conventional carriers are suitable, such as ceramic oxides and carbon, preferably $Al_2O_3$ such as γ- or δ- $Al_2O_3$, $SiO_2$, $ZrO_2$, $TiO_2$ (rutile, anatase) and mixed oxides thereof, carbon (apart from diamond), zeolites and silicalites such as titanium silicalite. The carriers may contain promoters to increase the catalytic activity and the sinter stability. Suitable promoters are alkali metals and alkaline earth metals, lanthanides and actinides. Preferred carriers are active carbon, silicon dioxide, aluminum oxide, titanium dioxide and zeolites.

The colloidal palladium can be applied as solution to the carrier. For this purpose, the carrier is impregnated with the colloidal solution of palladium. The impregnation can take place in a manner known per se by immersing the carrier in the solution or spraying with the solution. The impregnation can be followed by a drying step. The heterogeneous catalysts prepared in this way can be employed directly for the synthesis or can be calcined in another step. The calcination may involve elimination of the protective ligands without altering the particle sizes of the palladium clusters. The calcination generally takes place at from 100 to 600° C., preferably from 120 to 400° C., particularly preferably from 150 to 200° C.

However, the colloidal palladium can also be applied to the carrier by mixing it dry with the isolated colloidal palladium without diluent. A calcination step may likewise follow.

The palladium content of the heterogeneous catalysts is generally from 0.001 to 10% by weight, preferably 0.01 to 7% by weight, particularly preferably 0.03 to 5% by weight, and depends on the reactions to be carried out with these catalysts. The novel palladium-containing heterogeneous catalysts are suitable, like the colloidal palladium itself, for catalytic hydrogenations, especially for the abovementioned hydrogenation reactions. For this purpose, the palladium hydrogenation catalyst is for example dispersed in the olefin, acetylene, diene or saturated or unsaturated nitrile to be hydrogenated, and hydrogenation is effected at from 1 to 100 bar, preferably 1 to 10 bar, hydrogenation pressure.

The invention is explained in detail by the following examples.

EXAMPLE 1

Preparation of palladium clusters with triphenylphosphine as protective ligand 2.95 g of palladium(II) acetate and 5.6 g of triphenylphosphine are dissolved in 1 l of 3-methylbutanol under nitrogen and then stirred at 60° C. for 2 days. After the mixture has cooled, 5 times the amount of petroleum ether is added and the suspension is centrifuged at 5000 revolutions per min for 30 min. The supernatant brownish solution is decanted off and the product is dried in air. The black solid is redispersed in a mixture of water and pyridine (1:1).

The size distribution of the colloidal palladium was determined by measuring and counting the individual clusters on the transmission electron micrograph. This shows that the palladium clusters have, within limits, a uniform particle diameter of about 1.3 nm. The deviations are below the accuracy of measurement of about 0.1 nm.

EXAMPLE 2

Preparation of palladium clusters with phenanthroline as protective ligand 300 mg of palladium(II) acetate and 1900 mg of 1,10-phenanthroline are dissolved in 100 ml of 3-methylbutanol under nitrogen. The solution is heated at 60° C. for 7 days. After the solution has cooled, about 4 times the amount of petroleum ether is added and the mixture is centrifuged at 5000 rpm. The supernatant colorless solution is decanted off and the residue is dried in air. The black solid is redispersed in a mixture of water and pyridine (1:1).

According to the TE micrograph, about 80% of the palladium clusters have the same particle diameter of about 1.6 nm.

EXAMPLE 3

Preparation of a palladium-contaning heterogeneous catalyst

A colloidal solution of palladium prepared as in Example 2 is added dropwise to active carbon (Degusorb® from Degussa) suspended in the same solvent. After quantitative adsorption, which is evident from complete decolorization of the solution, the product is filtered and then dried under reduced pressure.

The catalytic activity of heterogeneous palladium clusters was examined on the basis of the catalytic hydrogenation of 2-hexyne.

EXAMPLE 4

100 mg of the catalyst from Example 3 are suspended in 25 ml of 2-hexyne. The suspension is saturated with hydrogen at 25° C. and 1 bar and stirred. After a reaction time of 2 h, 81% of the precursor are reacted, with a selectivity for hydrogenation to cis-2-hexene of 100%.

EXAMPLE 5

100 mg of the heterogeneous catalyst from Example 3 are calcined at 180° C. for about 5 hours. The calcined catalyst is suspended in 25 ml of 2-hexyne and saturated with hydrogen at 25° C. and 1 bar and stirred. After 2 h, 99% of the precursor has been converted to cis-2-hexene with a selectivity of 100%.

We claim:
1. Colloidal palladium composed of palladium clusters with an average particle diameter $0.2 \text{ nm} \leq d \leq 2 \text{ nm}$, wherein at least 80% of the palladium clusters have a particle diameter which differs by not more than 0.2 nm from the average particle diameter d, it being possible for the palladium clusters to have protective ligands on the surface.

2. Colloidal palladium as claimed in claim 1, wherein at least some of the palladium clusters have protective ligands on the surface, the protective ligands being able to coordinate with palladium.

3. Colloidal palladium as claimed in claim 2, wherein the protective ligands are phosphines and/or aromatic nitrogen compounds.

4. Colloidal palladium as claimed in claim 2, wherein the protective ligands are triphenyliphosphines, phenanthrolines or bipyridines.

5. A colloidal solution of palladium comprising colloidal palladium as claimed in claim 1.

6. A process for preparing a colloidal solution of palladium as defined in claim 5 by reacting a palladium salt with a reducing agent in a solution comprising the palladium salt, the reducing agent and a protective ligand at from 0 to 300° C., wherein a branched-chain alcohol having 4 to 30 carbon atoms, where the longest chain has 3 to 18 carbon atoms, is employed as reducing agent, and phosphines and/or aromatic nitrogen compounds are employed as protective ligands.

7. A process as claimed in claim 6, wherein palladium(II) acetate is employed as palladium salt.

8. A process as claimed in claim 6, wherein 3-methylbutanol is employed as solvent and reducing agent.

9. A process for preparing colloidal palladium, comprising the steps:
　a) preparing a colloidal solution of palladium by a process as claimed in claim 6;
　b) precipitating the colloidal palladium by adding a hydrocarbon solvent;

c) mechanically removing the colloidal palladium;

d) drying the colloidal palladium.

10. A method of use of colloidal palladium as defined in claim 1 for the hydrogenation of olefins, acetylenes, dienes and saturated and unsaturated nitriles comprising the step of redispersing the colloidal palladium in a liquid medium to give a colloidal solution of palladium.

11. A palladium-containing heterogeneous catalyst comprising colloidal palladium as defined in claim 1 applied to a carrier.

12. A palladium-containing heterogeneous catalyst as claimed in claim 11, wherein the carrier is selected from the group of $Al_2O_3$, $SiO_2$, $ZrO_2$, $TiO_2$ and mixed oxides thereof, carbon, zeolites and silicalites.

13. A process for preparing a palladium-containing heterogeneous catalyst as claimed in claim 12, comprising the steps:

a) preparing a colloidal solution of palladium by reacting a palladium salt with a reducing agent in a solution comprising the palladium salt, the reducing agent and a protective ligand at from 0 to 300° C., wherein a branched-chain alcohol having 4 to 30 carbon atoms, where the longest chain has 3 to 18 carbon atoms, is employed as reducing agent, and phoshpines and/or aromatic nitrogen compounds are employed as protective ligands;

b) impregnating a carrier selected from the group of $Al_2O_3$, $SiO_2$, $CrO_2$, $TiO_2$ and mixed oxides thereof, carbon, zeolites and silicalites with the colloidal solution of palladium;

c) drying the impregnated carrier, which can then be calcined.

14. A process as claimed in claim 13, wherein the carrier is impregnated by mixing the colloidal solution of palladium with a suspension of the carrier in the same solvent, and the carrier is subsequently removed mechanically.

15. A process for preparing a palladium-containing heterogeneous catalyst by mixing colloidal palladium as defined in claim 1 dry with a carrier as defined in claim 13, the resulting mixture possibly being subsequently calcined.

16. A method of use of the palladium-containing heterogeneous catalyst as defined in claim 11 for the hydrogenation of olefins, acetylenes, dienes and saturated and unsaturated nitriles comprising the step of dispersing the palladium-containing heterogeneous catalyst in the olefin, acetylene, diene or saturated or unsaturated nitrile to be hydrogenated.

* * * * *